United States Patent
Gournay et al.

(10) Patent No.: US 7,850,719 B2
(45) Date of Patent: Dec. 14, 2010

(54) SPINAL IMPLANT APPARATUS

(75) Inventors: Jose Gournay, en Goele (FR); Philippe Lemaitre, Alfortville (FR); Ezzine Banouskou, Villepinte (FR)

(73) Assignee: Warsaw Orthopedic, Inc., Warsaw, IN (US)

( * ) Notice: Subject to any disclaimer, the term of this patent is extended or adjusted under 35 U.S.C. 154(b) by 336 days.

(21) Appl. No.: 11/137,206

(22) Filed: May 25, 2005

(65) Prior Publication Data

US 2006/0106382 A1 May 18, 2006

(30) Foreign Application Priority Data

May 26, 2004 (FR) .................................. 04 05691
May 26, 2004 (FR) .................................. 04 05692

(51) Int. Cl.
*A61B 17/70* (2006.01)
(52) U.S. Cl. ................................................ 606/278
(58) Field of Classification Search ............ 606/60–61, 606/72–73, 246–279; 623/17.11; 403/53, 403/57, 58, 112–116, 122–144; 411/9, 170–171; 219/98
See application file for complete search history.

(56) References Cited

U.S. PATENT DOCUMENTS

| | | | |
|---|---|---|---|
| 1,697,037 A * | 1/1929 | Witz ........................... | 285/264 |
| 5,490,851 A | 2/1996 | Nenov et al. | |
| 5,628,740 A | 5/1997 | Mullane | |
| 5,649,926 A | 7/1997 | Howland | |
| 5,725,528 A | 3/1998 | Errico et al. | |
| 5,741,255 A * | 4/1998 | Krag et al. ..................... | 606/61 |
| 5,810,817 A | 9/1998 | Roussouly et al. | |
| 5,879,351 A | 3/1999 | Viart | |
| 6,077,263 A | 6/2000 | Ameil et al. | |
| 6,379,354 B1 * | 4/2002 | Rogozinski ................... | 606/61 |
| 6,716,213 B2 * | 4/2004 | Shitoto ........................ | 606/264 |
| 6,818,851 B2 * | 11/2004 | Ramasamy et al. ........... | 219/98 |
| 7,033,358 B2 * | 4/2006 | Taylor et al. .................. | 606/61 |
| 2003/0028191 A1 * | 2/2003 | Shluzas ........................ | 606/61 |
| 2004/0059332 A1 * | 3/2004 | Roussouly et al. ............ | 606/61 |
| 2004/0064140 A1 | 4/2004 | Taylor et al. | |
| 2004/0092931 A1 * | 5/2004 | Taylor et al. .................. | 606/61 |
| 2004/0177847 A1 * | 9/2004 | Foley et al. ................. | 128/95.1 |
| 2005/0033430 A1 * | 2/2005 | Powers et al. ............. | 623/17.11 |
| 2006/0229606 A1 * | 10/2006 | Clement et al. ............... | 606/61 |

FOREIGN PATENT DOCUMENTS

FR      2 716 794 A     9/1995
WO      WO 95/23559    9/1995

* cited by examiner

*Primary Examiner*—Thomas C Barrett
*Assistant Examiner*—Michael J Araj

(57) ABSTRACT

Orthopedic implants are disclosed that may be used in spinal applications. In one embodiment, a plate portion is provided with a threaded protrusion on which a connector for attachment to an orthopedic rod can be fitted. The protrusion may be multi-axially orientable with respect to said plate portion. The plate portion may include a dome having an inner surface that may be of conical shape, through which a portion of the protrusion may extend. A pin may be provided to retain the protrusion in place with respect to the dome. A second plate portion may be provided, which may be integral with or movable with respect to the first plate portion, that can be connected to a bone, e.g. iliac or sacral bone.

44 Claims, 10 Drawing Sheets

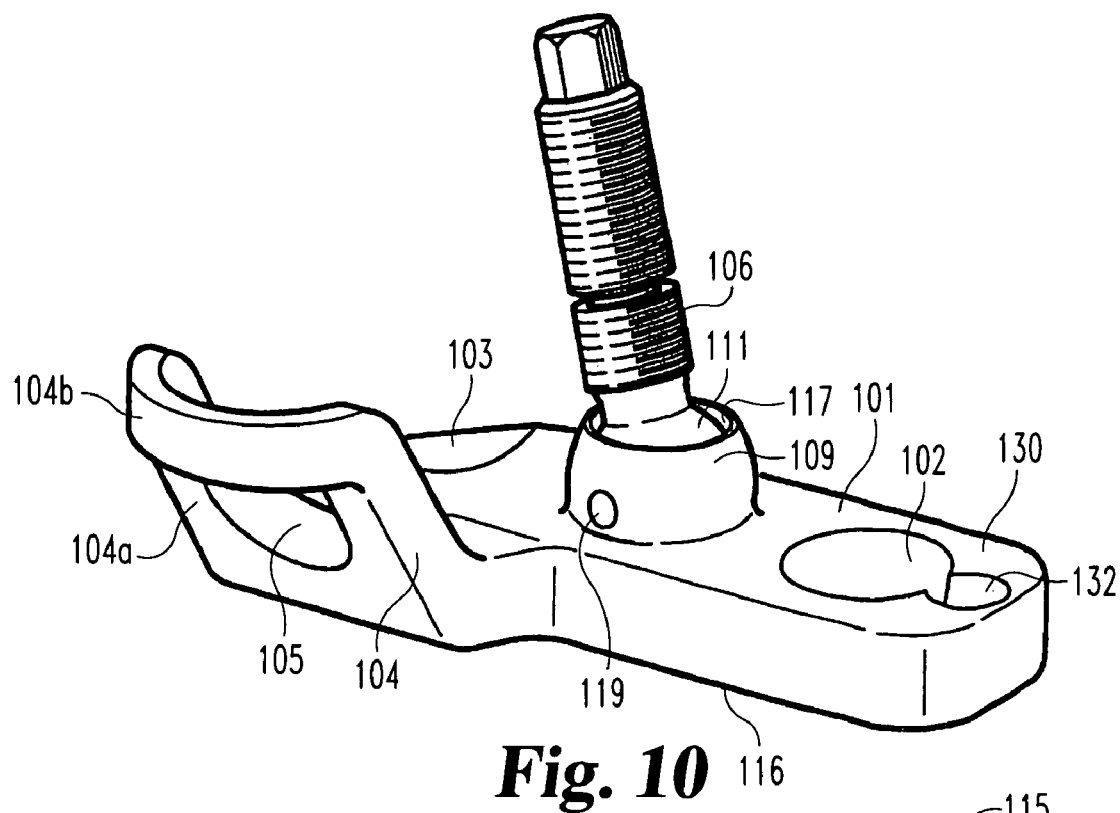
Fig. 10
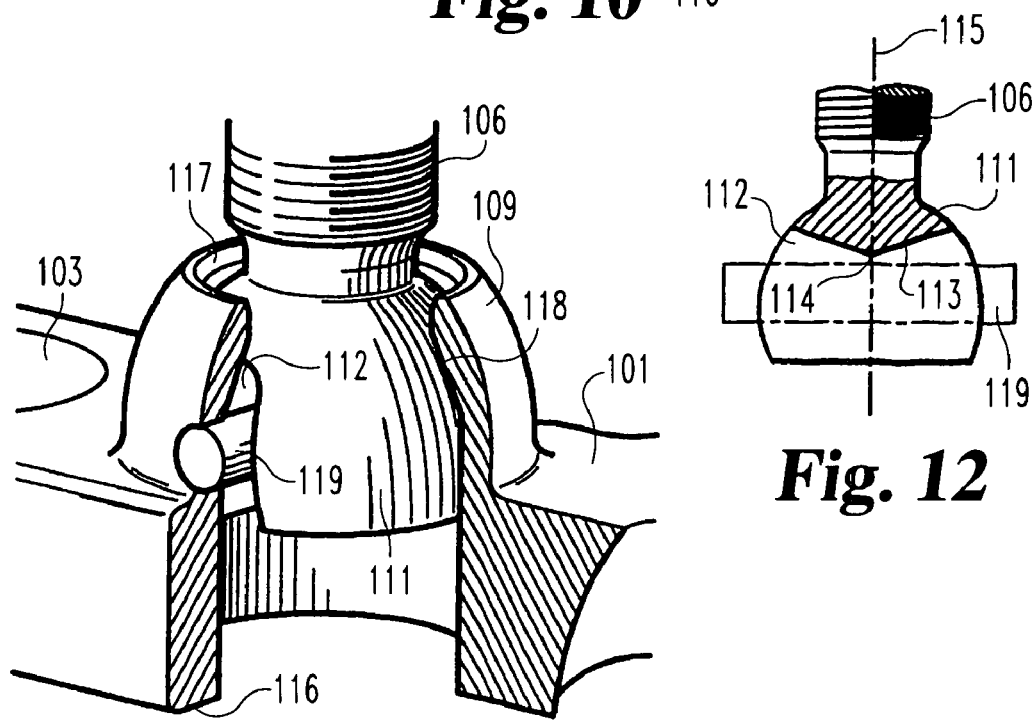
Fig. 11
Fig. 12

SPINAL IMPLANT APPARATUS

This application claims priority under 35 U.S.C. 119 to France Patent Application No. 04 05691, filed May 26, 2004, and to France Patent Application No. 04 05692, filed May 26, 2004.

BACKGROUND

Apparatus and systems for correcting deformations of the spine often comprise one or more rods extending along a portion of the spine. In the example of the sacral region of the spine, such rod(s) are usually fixed to the sacrum of the patient by way of a plate which, for instance, may straddle vertebrae S1 and S2 and bear a protrusion on which apparatus such as a slotted connector is fitted and immobilized. Such a slotted connector may be itself traversed by a rod and immobilize the latter by a wedging action. An example of such a plate is described in document WO-A-02/38061, for example.

It is also known to provide a plate which is fixed not on two vertebrae such as S1 and S2, but on one vertebra (for example S1) and on iliac bone of the patient. For this purpose, the plate may include, at one of its ends, a lateral extension provided with an orifice for the passage of a bone anchoring screw. This lateral extension is oriented in the direction of an iliac bone and is thus situated outside the plane of the plate, with which it normally forms an angle of the order of 50 degrees. In this way, the iliac bone can be connected to the rod. Different sizes of these sacral plates with iliac extension are available and are used in accordance with the morphology of the patient. However, the adaptation of the plate to the exact morphology of the patient is often only approximate.

BRIEF DESCRIPTION OF THE DRAWINGS

FIG. 10 shows a perspective view of another embodiment of an implant.

FIG. 11 shows a partial cutaway view in perspective of a portion of the embodiment of FIG. 10.

FIG. 12 shows a side view partially in section of a portion of the embodiment of FIG. 10.

DESCRIPTION OF THE ILLUSTRATED EMBODIMENTS

Figure 1:
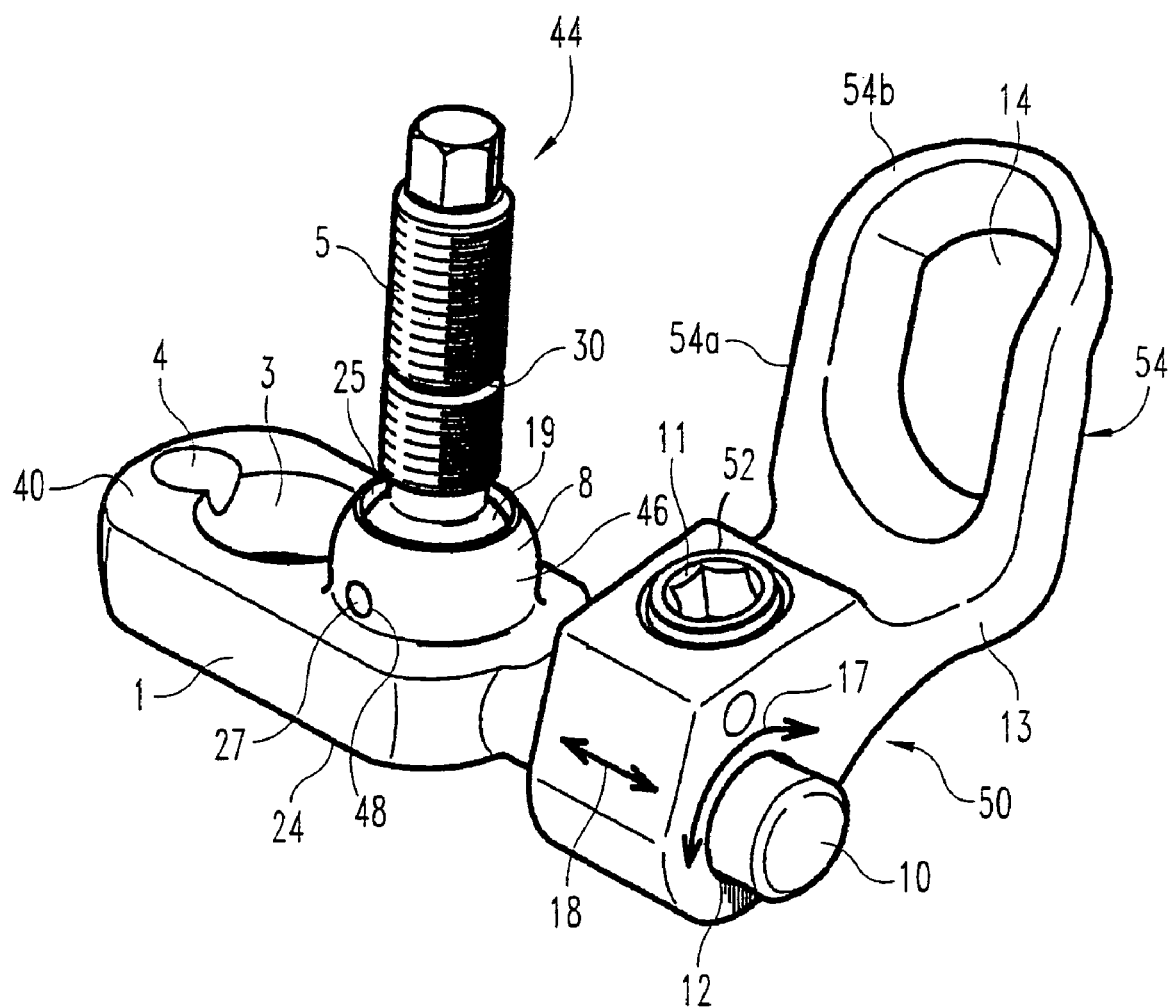
FIG. 1 shows a perspective view of an embodiment of an implant.
Figure 2:
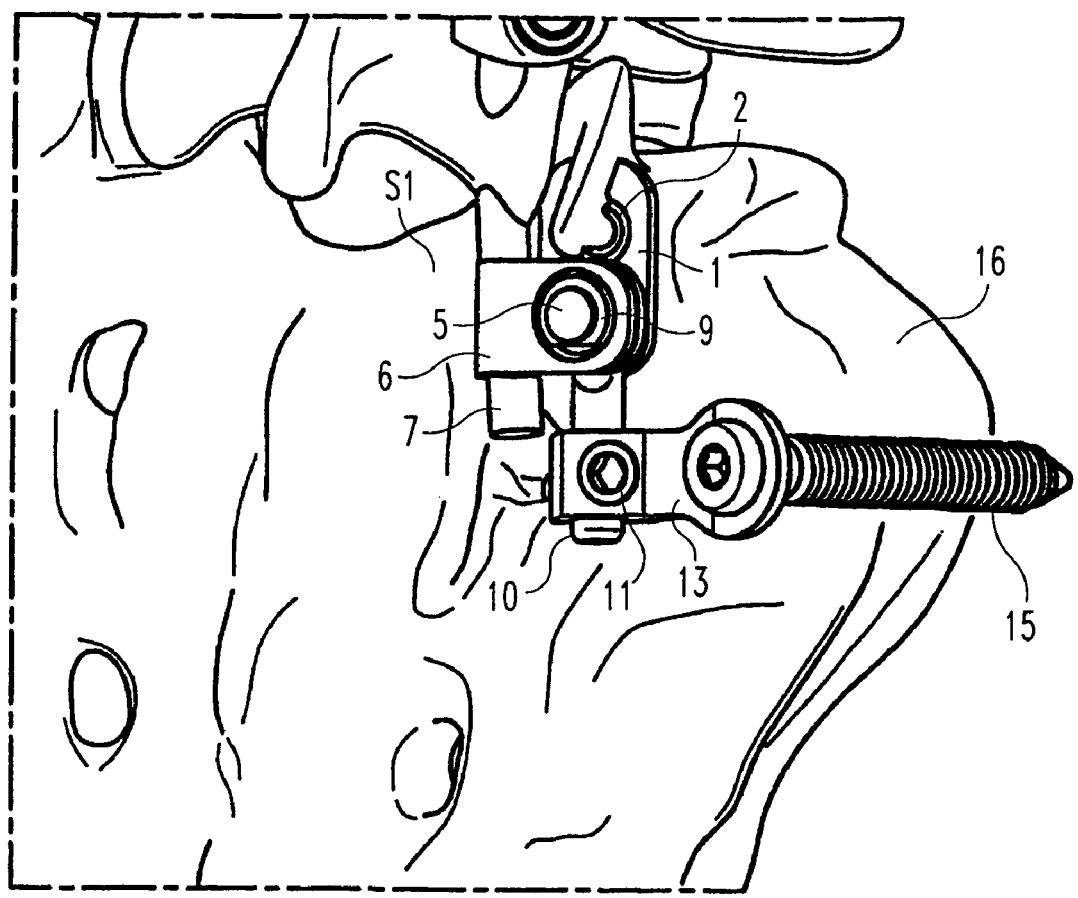
FIG. 2 shows a plan view of the embodiment of FIG. 1 mounted on the sacrum and iliac bone of a patient.
Figure 3:
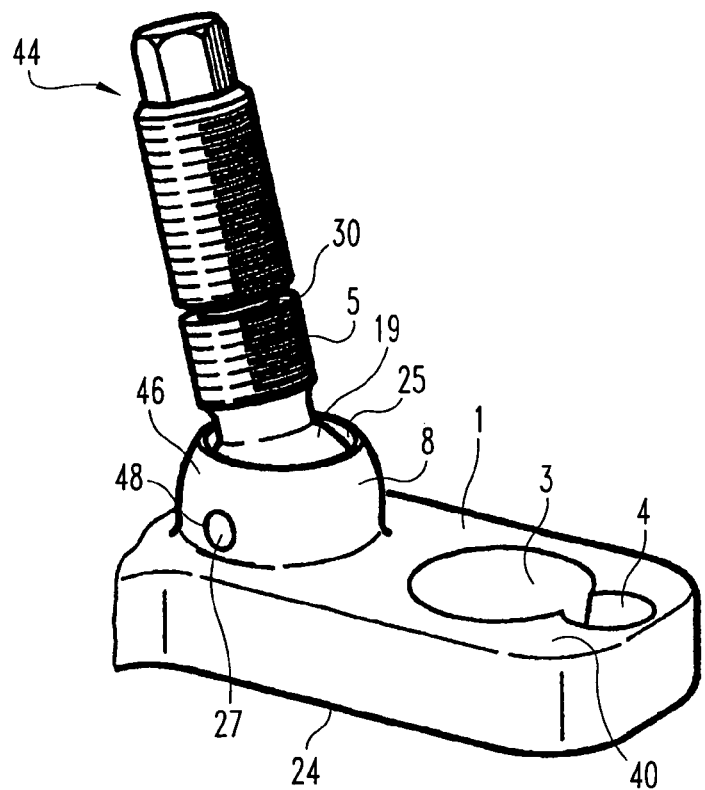
FIG. 3 shows a perspective view of a portion of the embodiment of FIG. 1.
Figure 4:
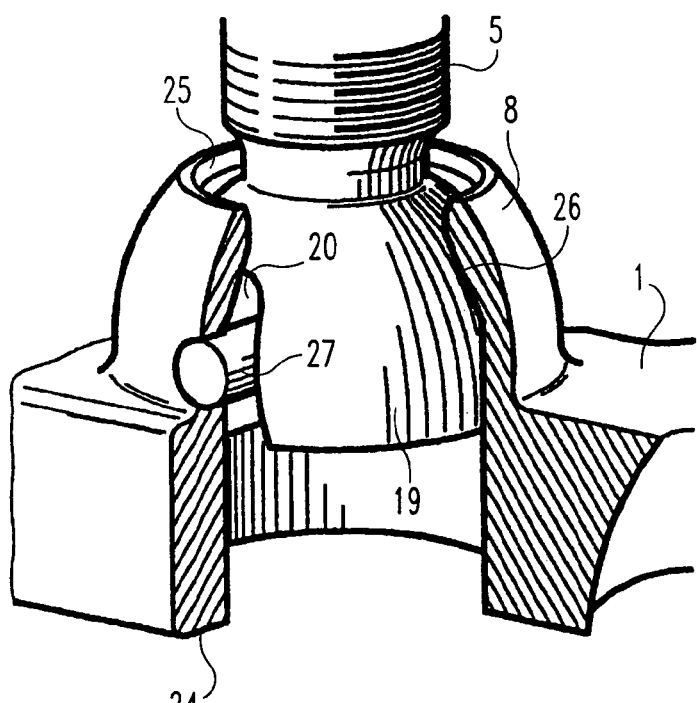
FIG. 4 shows a perspective view partially in section of a portion of the embodiment of FIG. 1.
Figure 5:
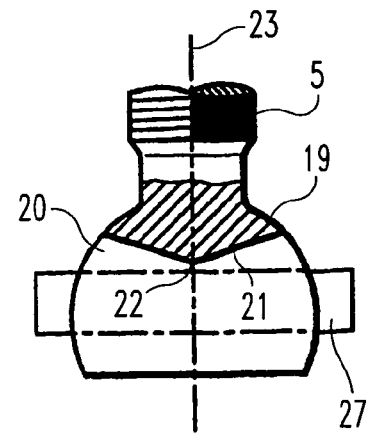
FIG. 5 shows a side view partially in section of a portion of the embodiment of FIG. 1.
Figure 6:
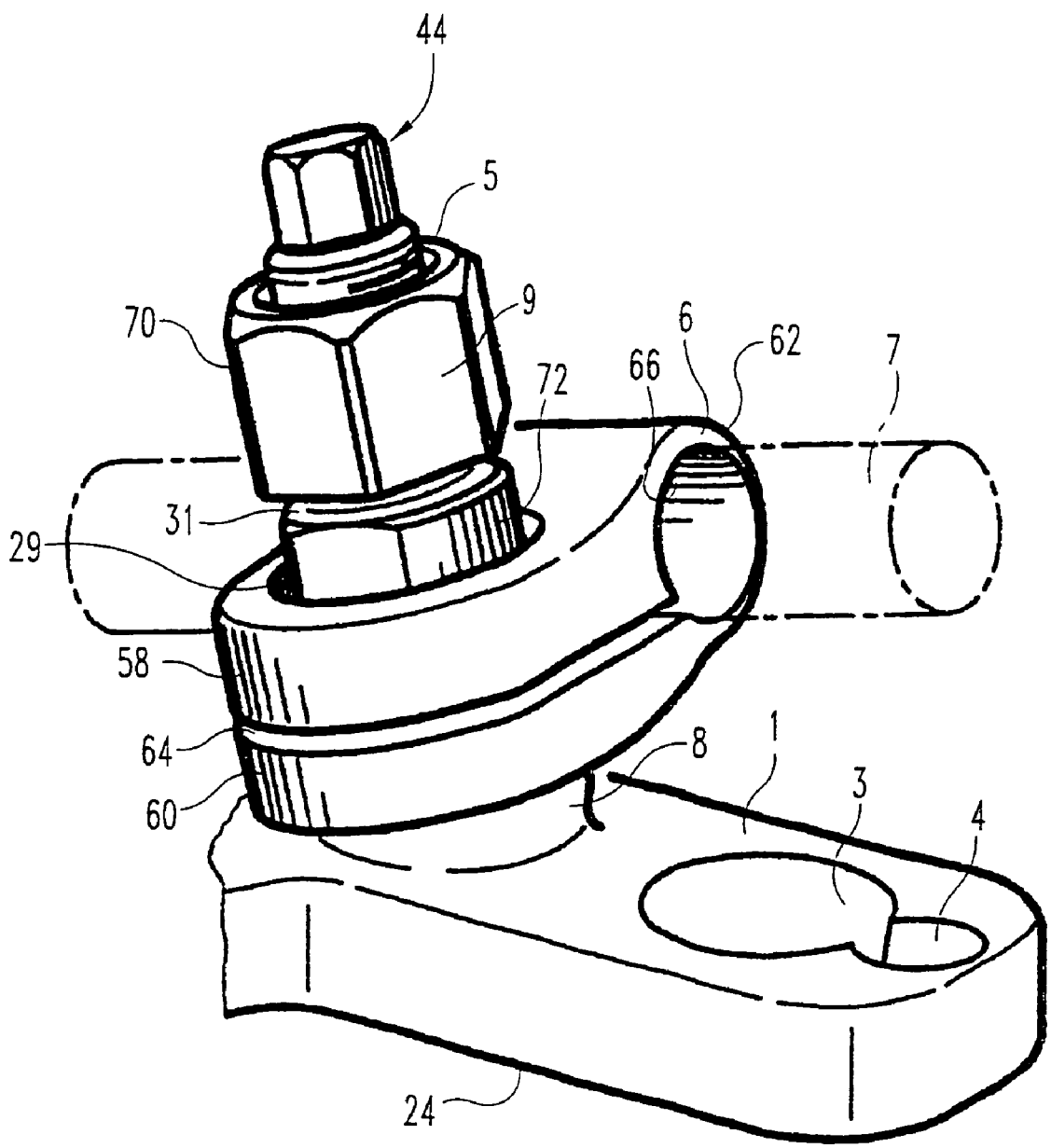
FIG. 6 shows a perspective view of a portion of the embodiment of FIG. 1 with embodiments of additional structure.

For the purposes of promoting an understanding of the principles of the invention, reference will now be made to the embodiment illustrated in the drawings and specific language will be used to describe the same. It will nevertheless be understood that no limitation of the scope of the invention is thereby intended. Any such alterations and further modifications in the illustrated device, and any such further applications of the principles of the invention as illustrated herein, are contemplated as would normally occur to one skilled in the art to which the invention relates.

Referring first generally to FIGS. 1 to 7, an embodiment of an implant is shown. In the illustrated embodiment the implant has two parts. Plate 1 that may be fixed on the sacrum of a patient, for example on vertebra S1. In the illustrated embodiment, plate 1 is oblong or elongated, and is fixed by means of a bone anchor 2, which may be a bone screw. Plate 1 includes an aperture 3, and in a particular embodiment includes a hole 4 that at least slightly overlaps aperture 3 and may be threaded. Anchor 2 passes through aperture 3 in plate 1 and into contact with bone. In embodiments having a threaded hole 4, a plug or screw (not shown) can be screwed in so as to immobilize the head of screw 2 and prevent it from migrating from its seat after placement. An upper surface 40 and a lower surface 24 of plate 1 may be substantially flat.

The illustrated embodiment of plate 1 also has a protrusion or shaft 5 and a dome 8. Shaft 5 has a longitudinal axis and is threaded in a particular embodiment, and a connector 6 can be fitted around at least a portion of shaft 5, as will be further described below. In the example shown, the lower part of protrusion 5 includes a spherical surface 19 and is traversed by a slot 20 substantially perpendicular to protrusion 5. As may be seen in FIG. 5, the illustrated embodiment of slot 20 is delimited by an upper surface 21 of V shape whose point 22 is situated substantially on the axis of symmetry 23 of protrusion 5. An upper part of shaft 5 includes a notch or line of lesser resistance 30 to enable shaft 5 to be relatively easily cut or broken, and a head portion 44. Head portion 44 may be configured hexagonally, as in the illustrated embodiment, or may include lobes, slots, internal prints or other configurations to permit gripping, holding, turning, and/or other manipulations.

Dome 8, in the illustrated embodiment, extends above upper surface 40 of plate 1 and has an outer surface 46 that is curved, and in a particular embodiment may form part of a sphere, and an inner surface 26 that is substantially conical in a particular embodiment. Dome 8 at least partially surrounds an orifice 25 that extends through plate 1, e.g. from a top edge of dome 8 through to lower surface 24 of plate 1. One or more holes 48 may be placed through dome 8, which holes 48 may extend from inner surface 26 all the way through dome 8 to outer surface 46. As will be discussed further below, shaft 5 is inserted into orifice 25 so that surface 19 of shaft 5 is adjacent to or contacting inner surface 26 of dome 8. In the illustrated embodiment, a pin 27 is also provided that is inserted through hole(s) 48 in dome 8 after shaft 5 is inserted through orifice 25. Pin 27 extends through slot 20 of shaft 5, and point 22 may be just above pin 27. In one particular embodiment, pin 27 has a diameter practically equal to the width of slot 20 to prevent any significant rotation of protrusion 5 about axis 23. Pin 27 inhibits protrusion 5 from falling out of orifice 25.

Protrusion 5 can be fixed, for example substantially perpendicular to the upper surface of plate 1 or, as in the example shown, it can be pivotable and/or of the type referred to as "multi-axial," that is to say capable of being oriented inside a cone whose angle may be of the order of 30 degrees. The means ensuring this multi-axial orientation can be of various types, and the illustrated example will be described in more detail below.

The illustrated embodiment of plate 1 also includes a longitudinal rod 10 extending therefrom, and which may be directed toward the lower part of the sacrum. Rod 10 may be substantially cylindrical and may be of any desired length or diameter compatible with spinal fixation. The embodiment shown depicts rod 10 to have a length comparable to or somewhat less than the length of plate 1, and a diameter comparable to or slightly larger than the distance between surfaces 40 and 24 of plate 1.

Lateral extension plate 13 connects to plate 1. In the illustrated embodiment, plate 13 includes a portion 50 having an orifice 12 sized and configured to accommodate at least part of rod 10 of plate 1, and an aperture 52 that intersects orifice 12. Aperture 52 may be threaded to accommodate a threaded plug or screw 11. Plate 13 also includes a portion 54 with an aperture 14 for accommodating a bone screw 15. Portion 54 is intended, in one particular embodiment, to lie adjacent to or contact an iliac bone 16 of a patient. Further, the illustrated embodiment of portion 54 includes two subparts 54*a* and 54*b*, each of which lie substantially in a plane, which planes are angled with respect to each other. The plane of part 54*a* is also angled with respect to portion 50. Thus, rod 10 of plate 1 may be inserted into orifice 12 of plate 13 and can be immobilized therein by threaded plug or screw 11 inserted through aperture 52. Aperture 14 of plate 13 permits implantation of screw 15 (FIG. 2) which penetrates into an iliac bone 16 of the patient in such a way as to fix plate 13 there.

Figure 7:
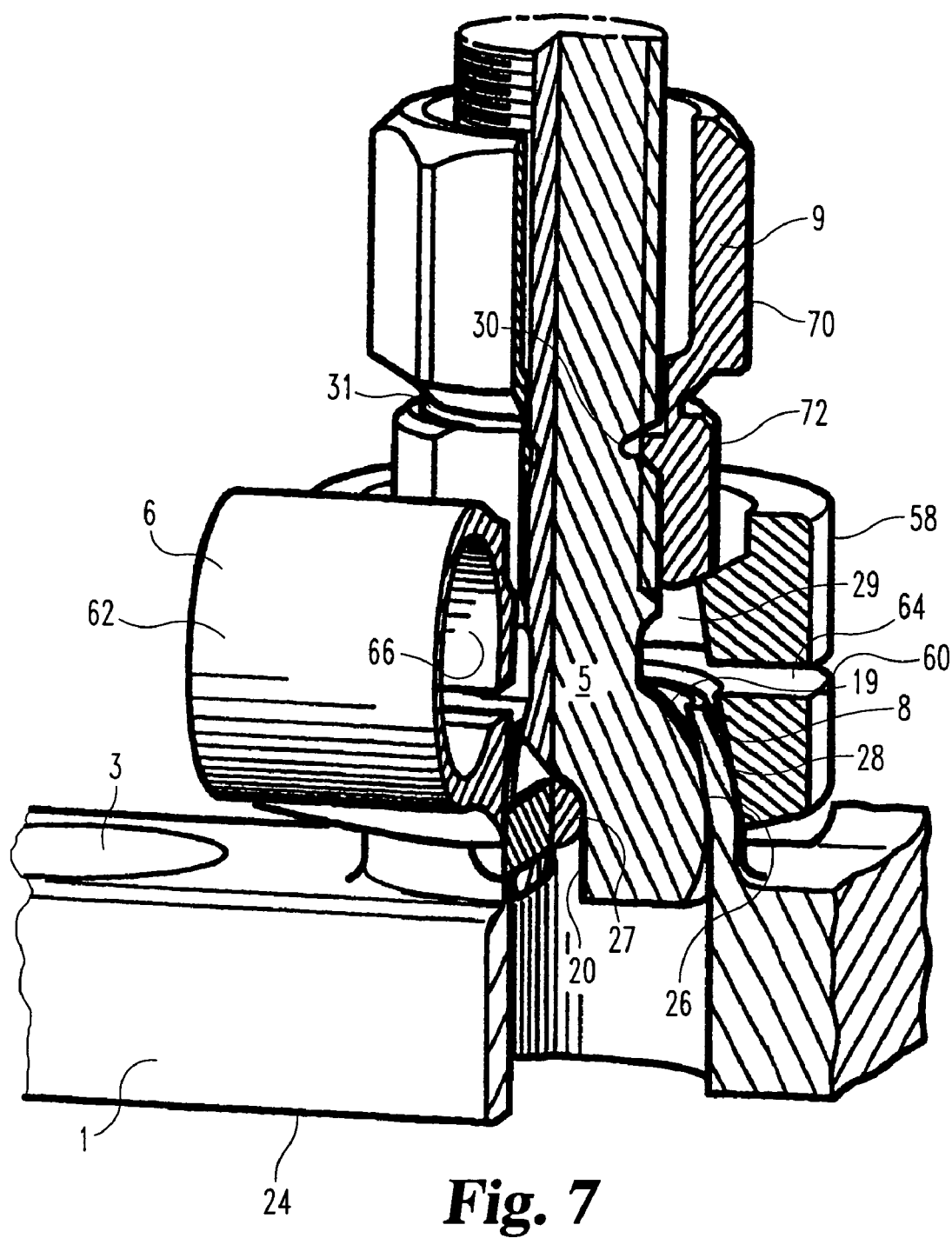
FIG. 7 shows a perspective view partially in section of the embodiments in FIG. 6.

The illustrated embodiment of connector 6 includes an upper portion 58 and a lower portion 60 that are connected by a joining portion 62. A slot 64 separates upper portion 58 and lower portion 60 in the normal or unstressed configuration. A channel 66 passes through connector 6. Channel 66 is sized and configured to accommodate at least a portion of spinal rod 7. Holes 29 are also provided through upper portion 58 and lower portion 60, and may be coaxial in a particular embodiment. In one specific embodiment, the contact between a spherical outer surface 46 of dome 8 and connector 6 is a sphere-to-cone contact. To that end, as seen in FIG. 7, holes 29 may have a conical internal surface 28. As will be discussed further below, connector 6 can be immobilized on dome 8, carried by plate 1, by means of a nut 9, which also closes slot 64 of connector 6 to allow connector 6 to clamp rod 7. Nut 9 includes an upper portion 70 and a lower portion 72 separated by a notch or line of lesser resistance 31.

To assemble the illustrated embodiment, protrusion 5 is engaged through the lower face 24 of plate 1 and is passed through an orifice 25 arranged at the summit of dome 8. Surface 19 of protrusion 5 thus comes into contact with inner surface 26 of dome 8. Pin 27 may then be fitted, which passes through dome 8 and comes to lie in slot 20 traversing the lower part of protrusion 5. As will be seen in FIG. 5, point 22 of the V-shaped upper surface delimiting slot 20 lies above pin 27, permitting only very slight vertical clearance of the protrusion 5 inside the dome 8 in this embodiment. Protrusion 5 can pivot around pin 27 to the degree permitted by dome 8, and can pivot in the plane defined by longitudinal axis 23 of protrusion 5 and pin 27 to the degree permitted by the depth of slot 20. The illustrated embodiment of pin 27 has a diameter practically equal to the width of slot 20, preventing any significant rotation of the protrusion 5 about its axis 23. These configurations of the lower part of the protrusion 5 and of the inner surface of the dome 8 provide for a complete multi-axial orientation of the protrusion 5 (typically inside a cone with an angle of about 30 degrees).

Plate 1 is connected to plate 13 by inserting rod 10 into and/or through orifice 12. Prior to locking down plug 11, plate 1 can be rotated with respect to plate 13, as indicated by arrows 17 (FIG. 1), and plate 1 can be translated longitudinally with respect to plate 13, as indicated by arrows 18 (FIG. 1). In this way, a particular relationship between plate 1 and plate 13 in terms of angle and distance can be made. Plate 13 is attached to bone, in a particular embodiment iliac bone, by inserting screw 15 through aperture 14 in plate 13 and into the bone. Plate 1 is attached to bone, in a particular embodiment sacral bone such as S1, by inserting screw 2 through aperture 3 in plate 1 and into bone. In embodiments having hole 4, a plug is placed in hole 4 to cover at least a portion of screw 2 to inhibit screw 2 from backing out, as previously noted.

Connector 6 is placed over shaft 5 so that shaft 5 is at least partially within holes 29 of connector 6. As has been discussed, in certain embodiments shaft 5 may be pivoted or otherwise moved to allow placement of connector 6, or once connector 6 has been placed to enable completion of the construct, or for other purposes of the surgeon. Nut 9 is threaded onto shaft 5 and tightened as the surgeon desires so that connector 6 is squeezed between nut 9 and dome 8 of plate 1. Such tightening causes connector 6 to clamp spinal rod 7, and also holds connector 6 and plate 1 together. Depending on the configuration given to connector 6, it may be possible, after tightening nut 9, either to return protrusion 5 automatically to an orientation substantially perpendicular to plate 1 (e.g. the multi-axial nature of protrusion 5 will thus have served only during implantation of the corrective apparatus), or to retain protrusion 5 in an orientation not perpendicular to plate 1, as seen in one embodiment in FIG. 6.

After such apparatus has been fitted in place, the surgeon generally removes those parts of protrusion 5 and of nut 9 which are redundant. For example, in one embodiment torque may be applied until a break occurs at notch 30 and/or 31, or notches 30 and 31 could serve as markers to cut their respective pieces. It is also possible to arrange such lines of lesser resistance on longitudinal rod 10 of plate 1 so that, if necessary, it is easy to shorten the part of rod 10 extending beyond plate 13. However, care must be taken to ensure that these lines of lesser resistance do not significantly impair the mechanical strength of rod 10 during the stresses to which it is subjected after the device has been fitted.

Figure 8:
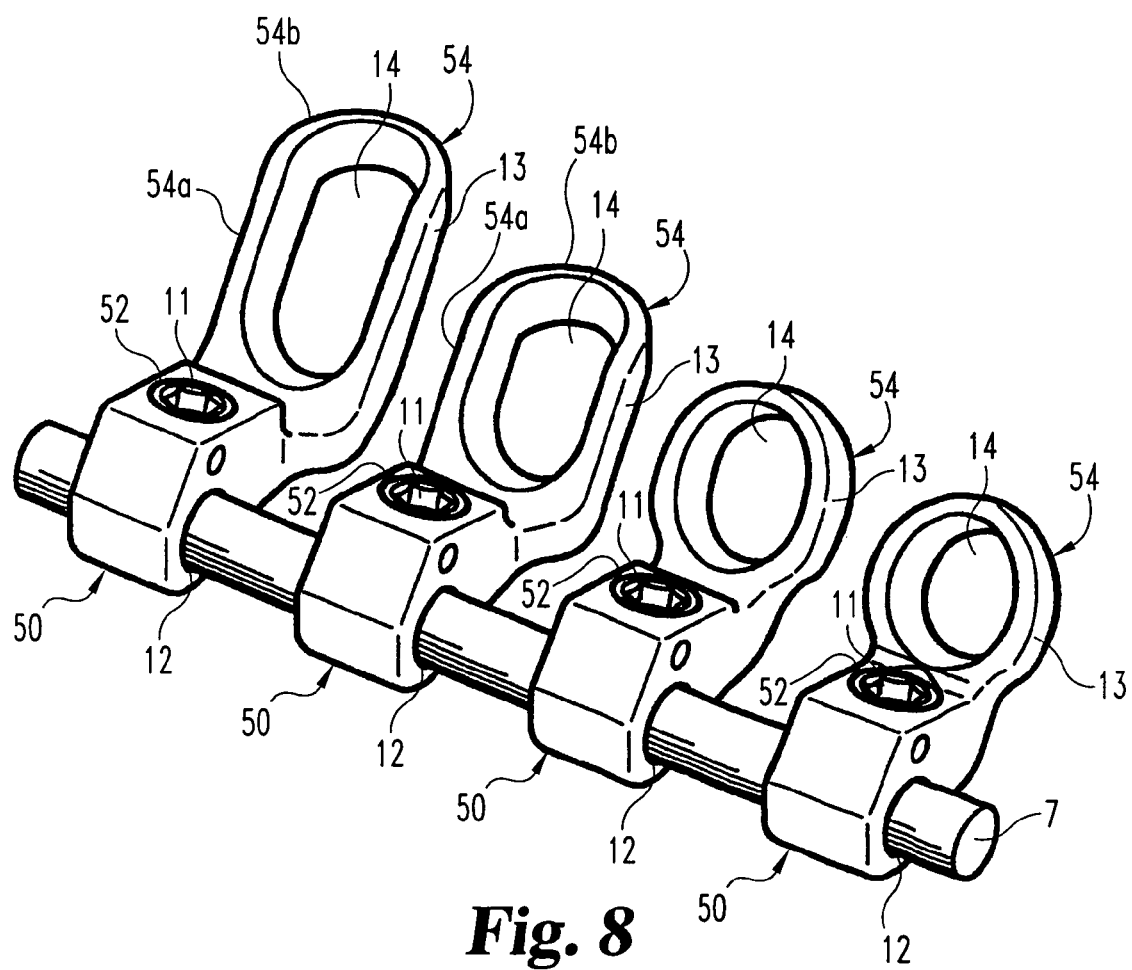
FIG. 8 shows a perspective view of a series of additional embodiments of part of the implant of FIG. 1.

Plate 13 may be provided in and chosen from several models with different geometries and sizes, such as those shown in FIG. 8, which are shown fitted on the same rod 7. These examples, showing apertures 14 that range from substantial elongation to substantially circular and some of which include the angled portion of plate 13 described above, are some of the configurations that might be provided so that the geometry of the implant can be optimally adapted to the particular morphology of the patient and to the exact site of fixation of the implant. With such models, it is possible to achieve a whole variety of implant geometries with the aid of a single model of plate 1.

Figure 9:
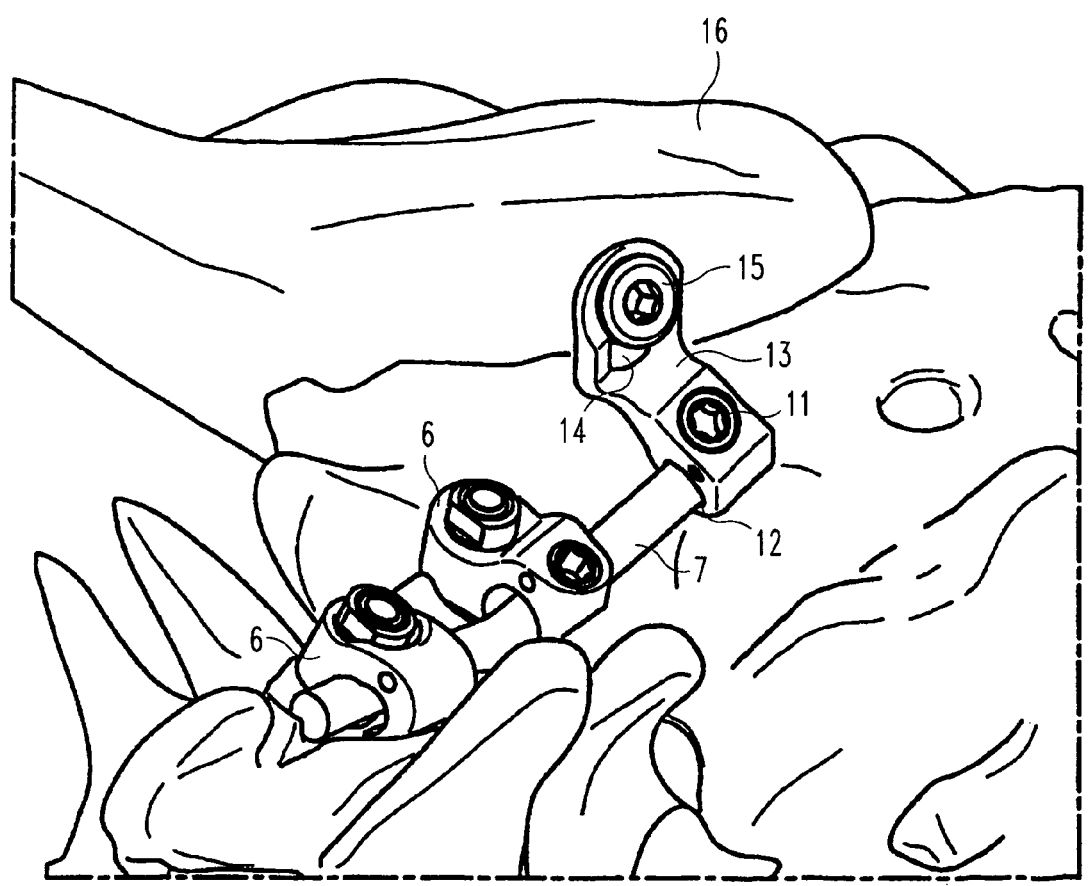
FIG. 9 shows a perspective view of another embodiment of an implant mounted on iliac bone and vertebra(e) of a patient.

In another embodiment, shown in FIG. 9, an implant is fixed on an iliac bone 16 by a screw 15, including a lateral extension plate 13 substantially as described above, in whose orifice 12 a spinal rod 7 is directly inserted. In the example shown, rod 7 is fixed to other parts of the spine by slotted connectors 6, mounted on protrusions carried by bone anchoring screws.

Turning now to FIGS. 10-14, a further embodiment of an implant including plate 101 is shown. Plate 101 may be a sacral plate, e.g. for implantation straddling vertebrae such as S1 and S2 of the patient. Plate 101 is fixed to these by two bone anchoring screws (not shown) which pass through orifices 102, 103 each formed at a respective end of plate 101. This embodiment of plate 101 includes a lateral extension 104 provided with an aperture 105 through which a bone anchoring screw (such as screw 15) may pass and penetrate into, for example, iliac bone of the patient. It must be understood, however, that the disclosure herein is applicable to any type of sacral plate, and generally to any type of element of a device for correcting spinal deformations which has a protrusion on which a connector can be fitted. It would in particular be applicable to a case where the protrusion is supported by a simple bone anchoring screw or by a hook.

Extension 104 is laterally positioned and integral with the remainder of plate 101 in the illustrated embodiment, having a longitudinal direction that in one particular embodiment is substantially perpendicular to a longitudinal direction of the remainder of plate 101. Extension 104 has a first portion 104a and a second portion 104b. In the illustrated embodiment, first portion 104a is substantially planar, and second portion 104b is substantially planar, and there is an angle between the planes of portions 104a and 104b. In addition, in the illustrated embodiment portion 104b is in a plane substantially parallel to upper surface 130 of plate 101, and aperture 105 is oblong or oval-shaped.

Figure 13:
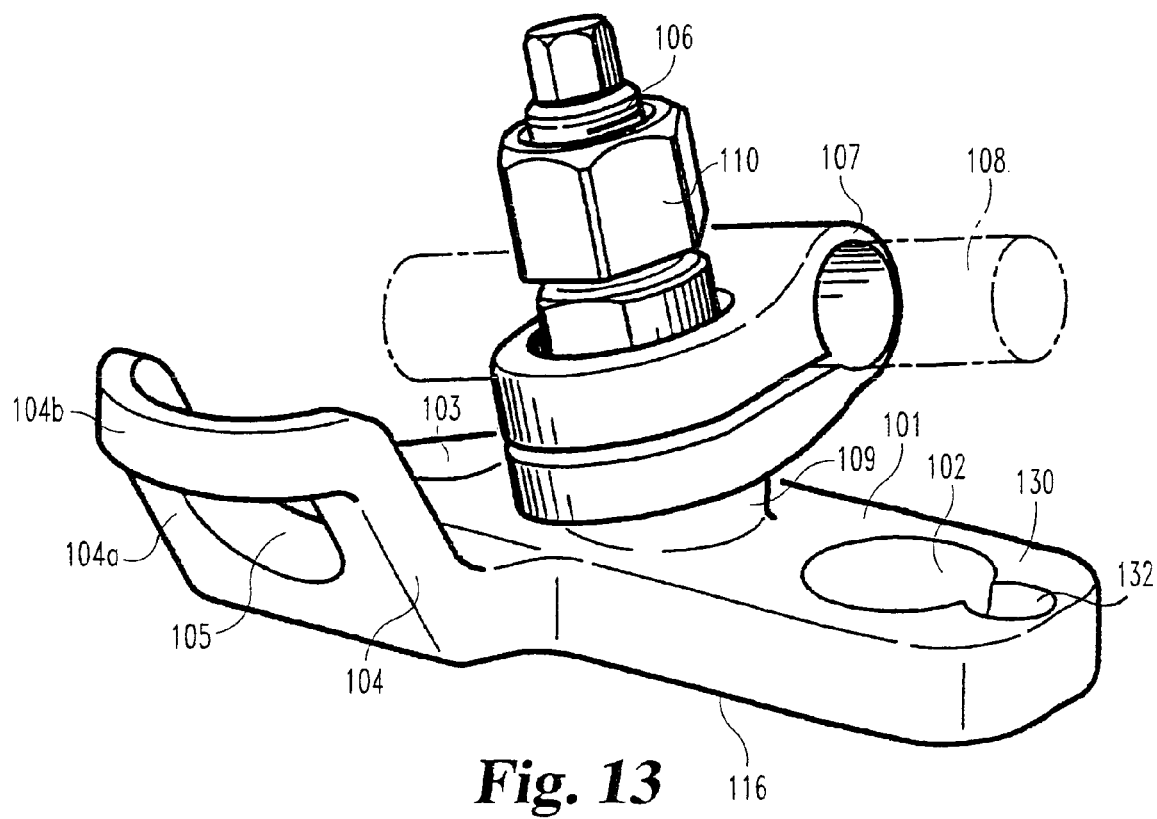
FIG. 13 shows a perspective view of a portion of the embodiment of FIG. 10 with embodiments of additional structure.
Figure 14:
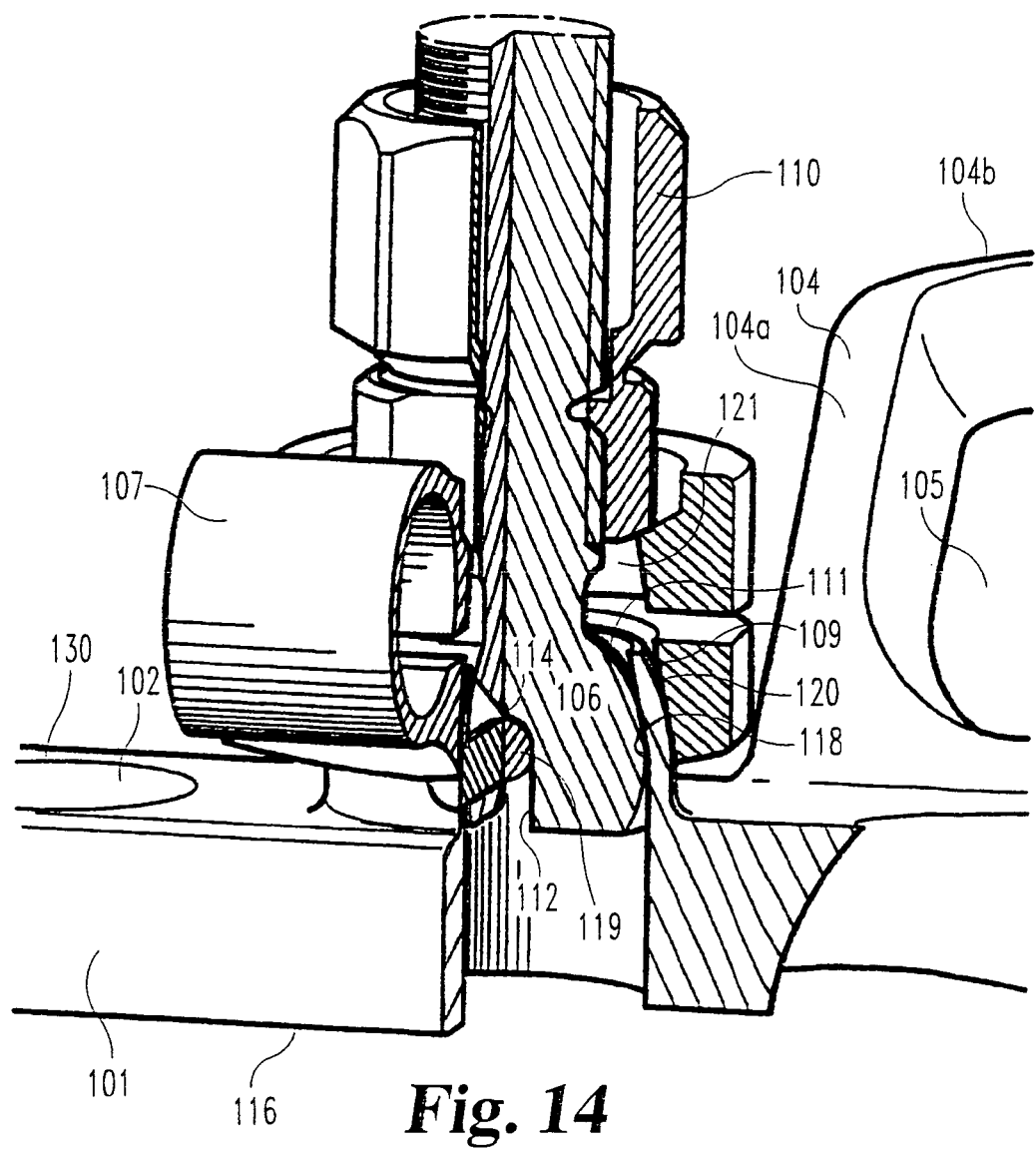
FIG. 14 shows a perspective view partially in section of the embodiments in FIG. 13.

Plate 101 includes several aspects that are similar or identical to the structures and methods discussed above with respect to the embodiment of plate 1. Plate 101 includes a protrusion 106 on which a connector 107 is to be fitted, which connector 107 is itself fitted on the rod 108 of the corrective device, the outline of which is represented in FIG. 13. The connector 107 is clamped on a spherical outer surface of a dome 109 formed on the upper surface of the plate 101. This clamping is done with the aid of a nut 110 screwed onto a thread present on the protrusion 106. The illustrated embodiments of protrusion 106, connector 107, dome 109 and nut 110 are essentially the same as protrusion or shaft 5, connector 6, dome 8 and nut 9 described above.

As with embodiments discussed above, protrusion 106 is engaged through the lower face 116 of plate 101 and is passed through an orifice 117 arranged at the summit of dome 109. Surface 111 of protrusion 106 thus comes into contact with inner surface 118 of dome 109. Pin 119 may then be fitted, which passes through dome 109 and comes to lie in slot 112 traversing the lower part of protrusion 106. As will be seen in FIG. 12, point 114 of the V-shaped upper surface 113 delimiting slot 112 lies above pin 119, permitting only very slight vertical clearance of the protrusion 106 inside the dome 109 in this embodiment. The illustrated embodiment of pin 119 has a diameter practically equal to the width of slot 112, preventing any significant rotation of the protrusion 106 about its axis 115.

Extension 104 is attached to bone, in a particular embodiment iliac bone, by inserting a screw (e.g. a bone screw such as screw 15 discussed above) through aperture 105 in extension 104 and into the bone. Plate 101 is further attached to bone, in a particular embodiment sacral bone such as S1, by inserting screws (e.g. bone screws such as screw 2 discussed above) through apertures 102 and 103 in plate 101 and into bone. In embodiments having hole 132 (similar or identical to hole 4 discussed above), a plug is placed in hole 132 to cover at least a portion of the screw in aperture 102 to inhibit the screw from backing out, as previously noted.

Connector 107 is placed over shaft 106 so that shaft 106 is at least partially within holes (e.g. holes 121 in FIG. 14) of connector 107. As has been discussed, in certain embodiments shaft 106 may be pivoted or otherwise moved to allow placement of connector 107, or once connector 107 has been placed to enable completion of the construct, or for other purposes of the surgeon. Nut 110 is threaded onto shaft 106 and tightened as the surgeon desires so that connector 107 is squeezed between nut 110 and dome 109 of plate 101. Such tightening causes connector 107 to clamp spinal rod 108, and also holds connector 107 and plate 101 together. For example, conical surface(s) 120 of connector 107 may be pressed against spherical surface 111 of shaft 106. Depending on the configuration given to connector 107, it may be possible, after tightening nut 110, either to return protrusion 106 automatically to an orientation substantially perpendicular to plate 101 (e.g. the multi-axial nature of protrusion 106 will thus have served only during implantation of the corrective apparatus), or to retain protrusion 106 in an orientation not perpendicular to plate 101, as seen in one embodiment in FIG. 13. The multi-axial nature of protrusion 106, in the illustrated embodiment, is substantially the same as that described above with respect to protrusion 5.

After such apparatus has been fitted in place, the surgeon generally removes those parts of protrusion 106 and of nut 110 which are redundant, as discussed above with respect to protrusion 5 and nut 9. Other manipulations may also be made by the surgeon, as discussed above.

Various modifications to the subject matter described above are possible. For example, for fixing the different parts of the implant on the spine or on an iliac bone, it would be possible to use means other than bone anchoring screws. As has been stated, the application of the invention is not limited to plates, but instead can also be applied to any element of an installation for correcting spinal deformations which comprises a protrusion for fitting a connector for which a temporary or permanent multiaxial orientation is sought.

While the invention has been illustrated and described in detail in the drawings and foregoing description, the same is to be considered as illustrative and not restrictive in character, it being understood that all changes and modifications that come within the spirit of the invention are desired to be protected.

What is claimed is:

1. An orthopedic implant, comprising:
   a first plate member having a longitudinal orifice, and an internally threaded hole communicating with said orifice, said first plate member also having a lateral extension provided with an aperture for the passage of a bone anchoring screw so that said first plate member can be fixed on an iliac bone;
   a second plate member having means for fixation on the sacrum, and also having a rod extending longitudinally, said rod adapted to be placed within said longitudinal orifice, and said second plate member having a threaded shaft connected thereto; and a threaded plug adapted to thread into said internally threaded hole and against said rod in said orifice;
   wherein said first plate member is adjustable relative to said second plate member in translation and rotation;
   further comprising a slotted connector for attachment to a spinal rod, said connector having an orifice for fitting said connector on said shaft, and a nut for threading onto said shaft for holding said connector on said second plate member and for clamping said connector around a spinal rod.

2. The apparatus of claim 1, wherein said connector orifice is substantially conical.

3. The apparatus of claim 1, wherein said nut has an upper portion and a lower portion separated by a line of lesser resistance, whereby said portions of said nut can be separated from one another by application of force to said line of lesser resistance.

4. The apparatus of claim 1, further comprising a rod at least partially within said orifice of said connector.

5. An ortho implant comprising:
a first plate member having a longitudinal orifice, and an internally threaded hole communicating with said orifice, said first plate member also having a lateral extension provided with an aperture for the passage of a bone anchoring screw so that said first member can be fixed on an iliac bone;
a second plate member having means for fixation on the sacrum, and also having a rod extending longitudinally, said rod adapted to be placed within said longitudinal orifice, and said second plate member having a threaded shaft connected thereto; and
a threaded plug adapted to thread into said internally threaded hole and against said rod in said orifice; and
wherein said shaft has a lower part with a surface at least part spherical and traversed by a slot, said slot delimited by an upper surface and two side surfaces extending from said upper surface and defining a width of said slot, said second plate member having a dome with an inner conical surface against which said lower part of said shaft can bear, and further comprising a pin connected to said dome and traversing at least part of said slot, said pin positioned proximately adjacent said upper surface of said slot.

6. The apparatus of claim 5, wherein said upper surface of said slot comprises a substantially V-shaped surface with a point of said V-shaped surface directed toward a lower end of said shaft and situated substantially along a longitudinal axis of said shaft.

7. The apparatus of claim 5, wherein said dome has an outer surface that is at least part spherical.

8. An orthopedic implant, comprising:
a first plate member having a longitudinal orifice, and an internally threaded hole communicating with said orifice, said first plate member also having a lateral extension provided with an aperture for the passage of a bone anchoring screw so that said first plate member can be fixed on an iliac bone;
a second plate member having means for fixation on the sacrum, and also having a rod extending longitudinally, said rod adapted to be placed within said longitudinal orifice, and said second plate member having a threaded shaft connected thereto; and
a threaded plug adapted to thread into said internally threaded hole and against said rod in said orifice; and
wherein said shaft has a lower part with a surface at least part spherical and traversed by a slot, said slot delimited by an upper surface and two side surfaces extending from said upper surface and defining a width of said slot, said second plate member having an opening through which at least part of said shaft extends.

9. The apparatus of claim 8, wherein said opening in said second plate member has an inner surface that is at least part conical.

10. The apparatus of claim 8, wherein said second plate member includes an opening having a dome at least partially surrounding said opening, and said shaft extends at least partially through said opening so that a part of said shaft is above said dome.

11. The apparatus of claim 10, wherein said opening in said second plate member has an inner surface that is at least part conical, said at least part conical surface of said second plate member engaged against said at least part spherical surface of said lower part of said shaft.

12. The apparatus of claim 8, wherein said second plate member includes an upper surface and an opposite lower surface, said opening extending through said second plate member from said upper surface to said lower surface, said opening through said lower surface sized to allow insertion of said lower part of said shaft therethrough, and said opening through said upper surface sized to allow passage of an upper part of said shaft therethrough, and further comprising a pin connected to said second plate member and extending at least partially across said opening and positioned adjacent said lower part of said shaft, wherein said pin engages said upper surface of said slot to substantially prevents said shaft from dropping out of said opening through said lower surface of said second plate member.

13. The apparatus of claim 12, wherein said second plate member includes a dome at least partially surrounding said opening, and said shaft extends at least partially through said opening in said upper surface of said second plate member so that a said upper part of said shaft is above said dome.

14. The apparatus of claim 13, wherein said opening in said second plate member has an inner surface that is at least part conical.

15. The apparatus of claim 8, wherein said second plate member and said rod are monolithic.

16. The apparatus of claim 8, wherein said slot extends transversely through said lower part of said shaft.

17. An orthopedic implant, comprising:
a first plate portion with a longitudinal axis, at least one hole for securing said first plate portion to a bone, and an opening surrounded at least in part by a dome and defining a dome aperture, said dome having an internal surface and an external surface;
a shaft connected to said first plate portion, said shaft having an upper part and a lower part, said lower part having a surface that is at least partially spherical and defining a slot, said slot delimited by an upper surface and two side surfaces extending from said upper surface and defining a width of said slot, said shaft extending through said dome aperture so that said surface of said lower part is adjacent to said internal surface of said dome, so that said shaft is multi-axially positionable relative to said first plate portion; and
a pin portion extending at least partially across said opening in said first plate portion, said pin portion at least partially traversing said slot and positioned proximately adjacent said upper surface of said slot; and
a second plate portion connected to said first plate portion, said second plate portion having a longitudinal axis substantially perpendicular to said axis of said first plate portion, said second plate portion having an aperture for a bone screw.

18. The apparatus of claim 17, wherein said second plate portion is integral with said first plate portion.

19. The apparatus of claim 17, wherein said first plate portion includes a plurality of holes for securing said first plate portion to a bone.

20. The apparatus of claim 17, wherein said plate portions are adjustable relative to one another.

21. The apparatus of claim 20, wherein said plate portions are adjustable relative to one another in translation and rotation.

22. The apparatus of claim 17, wherein said first plate portion includes a substantially flat part and a longitudinal rod connected to said substantially flat part, and wherein said second plate portion includes an elongated orifice adapted to accommodate said longitudinal rod, and wherein said longitudinal rod is at least partially inserted into said orifice so that said first plate portion and said second plate portion are rotationally and translationally adjustable.

23. The apparatus of claim 22, wherein said second plate portion includes a threaded hole intersecting said orifice, and further comprising a threaded plug adapted to thread within said threaded hole, whereby threading said plug into said hole and against said longitudinal rod locks said plate portions with respect to each other.

24. The apparatus of claim 22, wherein said first plate portion and said longitudinal rod are monolithic.

25. The apparatus of claim 17, wherein said shall is threaded, and further comprising a nut threaded on said shaft.

26. The apparatus of claim 25, wherein said nut has an upper portion and a lower portion separated by a line of lesser resistance, whereby said portions of said nut can be separated from one another by application of force to said line of lesser resistance.

27. The apparatus of claim 17, further comprising:
  a spinal rod; and
  a slotted connector for attachment to said spinal rod, said connector having an orifice for fitting said connector on said shall, and further comprising a locking member for connection with said shaft for holding said connector on said first plate member and for clamping said connector around said spinal rod.

28. The apparatus of claim 17, wherein said shaft extends along a longitudinal shaft axis, said upper surface of said slot comprising a substantially V-shaped surface with a point of said V-shaped surface situated substantially along said longitudinal shaft axis.

29. The apparatus of claim 17, wherein said second plate portion includes two substantially planar parts that are angled with respect to each other.

30. The apparatus of claim 17, wherein said aperture in said second plate portion is one of oblong and circular.

31. The apparatus of claim 17, wherein one of said plate portions includes a threaded hole overlapping an opening for a bone screw, and further comprising a set screw adapted to be threaded into said threaded hole, whereby said set screw inhibits backout of a bone screw in said opening for a bone screw.

32. The apparatus of claim 17, further comprising multiple versions of said second plate portion, whereby a surgeon may choose at least one of said versions for use based on a given morphology of a patient.

33. The apparatus of claim 17, wherein said first plate portion is adapted to be attached to a vertebral body, and said second plate portion is adapted to be attached to iliac bone.

34. The apparatus of claim 17, wherein said first plate portion has an upper surface and an opposite lower surface, said opening extending through said first plate portion from said upper surface to said lower surface, said opening through said lower surface sized to allow insertion of said lower part of said shaft therethrough, and said opening through said upper surface sized to allow passage of said upper part of said shaft therethrough.

35. The apparatus of claim 17, wherein said slot extends transversely through said lower part of said shaft.

36. The apparatus of claim 35, wherein said pin portion extends entirely across said opening in said first plate portion.

37. An orthopedic implant, comprising:
  a dome portion at least partially surrounding an opening defining a dome aperture, said opening having a surface that is at least part conical shape;
  a shaft having an upper part and a lower part, said lower part having a surface that is at least partially spherical and defining a slot, said slot delimited by an upper surface and two side surfaces extending from said upper surface and defining a width of said slot, said shaft extending through said dome aperture so that said surface of said lower part is adjacent to said surface of said opening, so that said shaft is multi-axially positionable relative to said dome; and
  a pin connected to said dome and extending at least partially across said opening, said pin at least partially traversing said slot of said shaft and positioned proximately adjacent said upper surface of said slot;
  wherein said dome is part of a plate, said plate having a hole for a bone screw offset from said dome and said shaft, and said plate further having a monolithic rod having a longitudinal axis, said dome and said bone screw hole being along said longitudinal axis.

38. The apparatus of claim 37, wherein said shaft extends along a longitudinal shaft axis, said upper surface of said slot having a substantially V-shape with a point of said V-shape directed towards the lower end of said shaft and situated substantially along said longitudinal shaft axis.

39. The apparatus of claim 37, wherein said implant is a bone screw.

40. The apparatus of claim 37, wherein said implant is a bone plate.

41. The apparatus of claim 40, wherein said implant is a sacral bone plate.

42. The apparatus of claim 37, wherein said plate has an upper surface and an opposite lower surface, said opening extending through said plate from said upper surface to said lower surface, said opening through said lower surface sized to allow insertion of said lower part of said shaft therethrough, and said opening through said upper surface sized to allow passage of said upper part of said shaft therethrough.

43. The apparatus of claim 37, wherein said slot extends transversely through said lower part of said shaft.

44. The apparatus of claim 43, wherein said pin extends entirely across said opening in said dome portion.

* * * * *

UNITED STATES PATENT AND TRADEMARK OFFICE
CERTIFICATE OF CORRECTION

PATENT NO.         : 7,850,719 B2
APPLICATION NO.    : 11/137206
DATED              : December 14, 2010
INVENTOR(S)        : Gournay et al.

Page 1 of 1

It is certified that error appears in the above-identified patent and that said Letters Patent is hereby corrected as shown below:

In Column 7, Line 6, in Claim 5, delete "ortho implant" and insert -- orthopedic implant, --, therefor.

In Column 7, Line 11, in Claim 5, delete "first" and insert -- first plate --, therefor.

In Column 7, Line 48, in Claim 8, delete "haying" and insert -- having --, therefor.

In Column 8, Line 15, in Claim 12, delete "prevents" and insert -- prevent --, therefor.

In Column 8, Line 22, in Claim 13, after "that" delete "a".

In Column 9, Line 14, in Claim 25, delete "shall" and insert -- shaft --, therefor.

In Column 9, Line 25, in Claim 27, delete "shall," and insert -- shaft, --, therefor.

Signed and Sealed this
Twenty-sixth Day of April, 2011

David J. Kappos
*Director of the United States Patent and Trademark Office*